United States Patent [19]

Khanna et al.

[11] Patent Number: 5,032,503
[45] Date of Patent: Jul. 16, 1991

[54] LIQUID SINGLE REAGENT FOR AIR ENZYME COMPLEMENTATION ASSAY

[75] Inventors: Pyare L. Khanna, Fremont; Stephen B. Friedman, Green Valley Suisun; David S. Kates, Davis, all of Calif.

[73] Assignee: Microgenics Corporation, Concord, Calif.

[21] Appl. No.: 209,916

[22] Filed: Jun. 22, 1988

[51] Int. Cl.$^5$ ............ G01N 33/535; G01N 33/542; G01N 33/566

[52] U.S. Cl. .................. 435/7.6; 435/7.8; 435/18; 435/961; 435/962; 435/963; 435/975; 436/500; 436/501; 436/505; 436/537; 436/826

[58] Field of Search ............ 435/7, 14, 810, 825, 435/826, 184, 188, 7.6, 7.8, 961, 962, 963, 975, 18; 436/826, 500, 501, 505, 537, 815

[56] References Cited

U.S. PATENT DOCUMENTS

| | | |
|---|---|---|
| 4,121,975 | 10/1978 | Ullman et al. |
| 4,447,527 | 5/1984 | Monte et al. ............... 435/7 |
| 4,708,929 | 11/1987 | Henderson ............... 435/7 |
| 4,786,591 | 11/1988 | Draeger et al. ............... 435/7 |

FOREIGN PATENT DOCUMENTS

| | | |
|---|---|---|
| 0243001 | 3/1987 | European Pat. Off. |
| 0286367 | 4/1988 | European Pat. Off. |
| 0085290 | 5/1984 | Japan . |
| 0160884 | 8/1985 | Japan . |
| 8300876 | 3/1983 | PCT Int'l Appl. ............... 435/14 |

OTHER PUBLICATIONS

A. Hersey et al., J. Chem. Soc., Faraday Trans 1, 1986, 82: 1271–1287, Mechanism of Inclusion-Compound Formation for Binding of Organic Dyes, Ions, and Surfactants to α-Cyclodextrin by Kinetic Methods & Based on Competition Ex. Short Communication, Effects of Detergents on the Hydrolysis of Glycolipids by β-Galactosidase.

Daniel R. Henderson et al., Clinical Chemistry (1986) 32: 1637–1641, CEDIA TM, a New Homogeneous Immunoassay System.

Dimitriadix, Giorgios J., "Effect of Detergents on Antibody-Antigen Interaction", in *Analytical Biochemistry* (1979) 98: 445–451.

Chemical Abstracts, vol. 106, No. 3, Jun. 19, 1987, p. 645, Ab. 106: 18963h, Hersey et al., "Mechanism of Inclusion ... ".

Chemical Abstracts, vol. 104, No. 15, Apr. 14, 1986, Ab. 104: 125872h, Bachas et al., "Binding Proteins as ... ".

*Primary Examiner*—David A. Saunders
*Attorney, Agent, or Firm*—Richard L. Neeley

[57] ABSTRACT

A method is provided for combining normally interacting reagents in a liquid single reagent and preventing complex formation using a surfactant and then reversing the inhibition by adding a cyclodextrin. The method finds particular use in diagnostic immunoassays. Reagents facilitating the invention are also provided.

34 Claims, No Drawings

LIQUID SINGLE REAGENT FOR AIR ENZYME COMPLEMENTATION ASSAY

INTRODUCTION

1. Technical Field

The present invention relates to immunoassay reagents, and, in particular, to reagents for competitive inhibition assays.

2. Background of the Invention

A wide variety of immunoassays have been based on competitive inhibition where analyte in the sample competes for a fixed amount of anti-analyte antibody with a known amount of analyte, usually labeled analyte, present in the assay medium. Enzyme labels are often used in competitive inhibition assays, where binding of anti-analyte antibody with an enzyme-analyte conjugate changes, usually decreases, the rate of enzyme-catalyzed breakdown of substrate.

A number of such assays have been based on the ability of fragments of β-galactosidase to complement and form active enzyme. In particular, a β-galactosidase enzyme donor (ED) combines with a β-galactosidase enzyme acceptor (EA) to form active β-galactosidase enzyme. Conjugating a small analyte or an analyte analogue to the ED at certain sites does not affect the rate of β-galactosidase catalyzed activity. However, when the ED-analyte conjugate is bound by anti-analyte antibody, the enzyme-catalyzed reaction rate during the initial phase of the reaction is reduced This reduction in enzyme-catalyzed reaction rate has been used to quantitate the determination of a plurality of analytes where ED-analyte conjugate present in a assay medium and analyte present in the sample compete for anti-analyte antibody prior to the addition of EA. The β-galactosidase-catalyzed reaction rate increases as the amount of analyte present in the sample increases.

With competitive assays, the labeled analyte and anti-analyte antibody generally cannot be mixed prior to addition of the sample. In complementation assays, usually the ED and EA are separated until after incubation of ED-analyte conjugate and sample with anti-analyte antibody. This necessitates careful delivery by the end user of any reagent in the assay used in limiting quantity. Further, such assays are not readily adaptable to automation since most analyzers dispense only a single analyte-specific reagent and a common reagent to each sample well.

Relevant Literature

Modified β-galactosidase enzyme donors and enzyme acceptors have been prepared by chemical synthesis and recombinant engineering. The modified fragments retain β-galactosidase activity upon complementation and facilitate production of and attachment of analyte to the fragments. See for example U.S. Pat. No. 4,708,929 and the articles cited therein.

Cyclodextrins are commercially available and are well known compounds which form inclusion compounds (clathrates) which are capable of trapping a number of organic molecules. For a description of their properties and methods of production, see, for example, Bender et al., Cyclodextrin Chemistry, Springer-Verlag, New York, 1978 (a 96-page book); French, *Adv. Carbohydr. Chem.* (1957) 12:189-260; Thoma et al., Starch: Chemistry and Technology, Vol. 1, Whistler et al., Eds., Academic Press, New York, 1965, pp. 209-249; and Cramer et al., *Naturwiss.* (1967) 154:625-635. The compounds are naturally occurring and are obtained from the action of *Bacillus macerans* amylase on starch.

EPO application No. 87302511.8 to Gibbons et al. Publication No. 0 243 001 describes a single reagent assay method wherein a specific binding pair (sbp) member is reversibly confined in a material that temporarily renders the confined sbp member incapable of binding with its complementary member. In a preferred embodiment, an enzyme-hapten conjugate is confined in a liposome and the assay reaction is initiated by the addition of a surfactant.

SUMMARY OF THE INVENTION

A method is provided for combining normally interacting reagents in a liquid single reagent and preventing complex formation using a surfactant and then reversing the inhibition by adding a cyclodextrin. The method finds particular use in diagnostic immunoassays. Reagents facilitating the invention are also provided.

DESCRIPTION OF THE SPECIFIC EMBODIMENTS

A method is provided wherein reaction of complementary members of a specific binding pair to form a specific binding pair complex is reversibly inhibited by use of a surfactant. Reaction is then initiated by adding a cyclodextrin. The method can be used any time it is desirable that a mixture of the complementary members of a specific binding pair are combined prior to initiation of complex formation. The method finds particular application in diagnostic assays.

The method comprises providing, in a process which uses complex formation between complementary members of a specific binding pair, a prepared liquid single reagent comprising a reaction-inhibiting amount of a surfactant and the complementary members of the specific binding pair. In performing the process, a sufficient amount of a cyclodextrin is added to the single reagent to allow complex formation.

The liquid single reagent may be employed whenever combining the complementary members of a specific binding pair without initiating complex formation is desirable, since the inhibition is reversible. This reversible inhibition of complex formation will be desirable whenever accurate measurement of the complementary members of a specific binding pair is required, such as where one or both members are present in limiting quantity. The method finds application in diagnostic assays where one or both complementary members of a specific binding pair are combined with the sample in an assay medium as a first step of an assay procedure. In accordance with the subject invention, the components which are to be mixed with the sample can be provided as a liquid single reagent where the complementary members of a specific binding pair are combined without initiating complex formation. Other than eliminating measurement steps and adding the cyclodextrin solution to initiate complex formation, the assay methods, conditions and reagents using the single reagent formulation will not differ significantly from those of the prior art.

As stated previously, the liquid single reagent comprises a reaction-inhibiting amount of a surfactant and the complementary members of a specific binding pair. Other components of the assay medium, e.g. enzyme substrate, buffer solution, etc. may also be included in the liquid single reagent composition. These additional components may vary depending on the particular assay protocol. Stabilizers, bactericides or preservatives which do not interfere with the function of the assay components may also be present. While the liquid single reagent will be used in liquid form in an assay, the liquid single reagent may be provided as a liquid or dried or lyophilized to form a powder. The powder composition can be formulated to be reconstituted in buffer, water or the sample, depending on the assay.

The liquid single reagent may be used in an assay method to quantitate any analyte determined by prior art immunoassay or complementation methods including proteins, drugs, polynucleotides, or polysaccharides. The method can be used with any aqueous sample containing the analyte. The analyte may be a small analyte, a hapten, present in a bodily fluid, usually in patient serum, plasma, saliva, urine, or whole blood, or a larger analyte such as proteins. Sample pretreatment will follow conventional procedures.

Numerous specific binding pairs which may find use in diagnostic assays are known. Usually, at least one of the complementary members of the specific binding pair will be a protein or protein fragment, e.g. enzyme donor/enzyme acceptor, antigen/antibody, lectin/sugar, etc. Many competitive inhibition assays use a known amount of an analyte reagent, usually a labeled analyte, that competes with analyte present in the sample for a predetermined amount of the reciprocal binding pair member. As the receptor, an antibody will usually be employed, either polyclonal or monoclonal. Alternatively, a receptor which specifically binds an analyte can be used in place of antibody, e.g. vitamin B12-intrinsic factor, thyroxin-thyroxine binding globulin, and folic acid-folate binding protein. Either member of the specific binding pair may be bound to a label. The label may be an enzyme, fluorescer, dye, substrate, or chemiluminescer. Desirably the label is an enzyme bound to the analyte or an analyte analogue to produce an enzyme-analyte conjugate.

There are a number of surfactants which may be used to prevent the reactions of complementary members of a specific binding pair and which can be neutralized by a cyclodextrin. For example, a number of biological detergents (surfactants) are listed as such by Sigma Chemical Company on pages 316-321 of its 1988 Catalog of Biochemical and Organic Compounds. Such surfactants are divided into four basic types: anionic, cationic, zwitterionic, and nonionic. Examples of anionic detergents include alginic acid, caprylic acid, cholic acid, 1-decanesulfonic acid, deoxycholic acid, 1-dodecanesulfonic acid, N-lauroylsarcosine, and taurocholic acid. Cationic detergents include dodecyltrimethylammonium bromide, benzalkonium chloride, benzyldimethylhexadecyl ammonium chloride, cetylpyridinium chloride, methylbenzethonium chloride, and 4-picoline dodecyl sulfate. Examples of zwitterionic detergents include 3-[(3-cholamidopropyl)-dimethylammonio]-1-propanesulfonate (commonly abbreviated CHAPS), 3-[(cholamidopropyl)-dimethylammonio]-2-hydroxy-1-propanesulfonate (generally abbreviated CHAPSO), N-dodecyl-N,N-dimethyl-3-ammonio-1-propanesulfonate, and lyso-α-phosphatidylcholine. Examples of nonionic detergents include decanoyl-N-methylglucamide, diethylene glycol monopentyl ether, n-dodecyl β-D-glucopyranoside, polyoxyethylene ethers of fatty acids (particularly $C_{12}$-$C_{20}$ fatty acids, (e.g., sold under the trade name Triton), ethylene oxide condensates of fatty alcohols e.g. sold under the name Lubrol), polyoxyethylene sorbitan fatty acid ethers (e.g., sold under the trade name Tween), and sorbitan fatty acid ethers (e.g., sold under the trade name Span).

The surfactant will be present in the liquid single reagent in a concentration at least sufficient to inhibit complex formation between the complementary members of a specific binding pair. Desirably, the concentration will be insufficient to denature the specific binding pair members, the sample analyte or any other assay reagents. In any case the surfactant effects will be reversed by use of a cyclodextrin and the assay medium components will not be permanently denatured. A preferred surfactant is a nonionic detergent, desirably polyoxyethylene esters of fatty acids, particularly $C_{12}$-$C_{20}$ fatty acids, (e.g., sold under the trade name Triton), which is used at about 0.2% to about 1.0% (w/w), usually about 0.2% to about 0.5% (w/w), of the liquid single reagent formulation.

Cyclodextrins are cyclic amyloses. Three types are known: a cyclohexaamylose (α-cyclodextrin), a cycloheptaamylose (β-cyclodextrin), and a cyclooctaamylose (γ-cyclodextrin). Although all three of the cyclodextrins are effective in removing surfactants, advantages are achieved by matching the size of the portion of the surfactant complexed in the available interior space of the cyclodextrin. Large surfactants defining a relatively large molecular volume, such as those derived from cholic acid, are therefore most readily removed using γ-cyclodextrin, which has the largest interior space. Smaller surfactants, such as fatty acid salts and fatty sulfonates, which are elongated chains having a relatively small molecular cross-section, are most readily removed with α-cyclodextrin, which has the smallest interior space of the three cyclodextrins.

The use of a sufficient amount of a cyclodextrin reverses surfactant-induced inhibition of complex formation, thus neutralizing the surfactant, and allows complex formation between the specific binding pair members. It is preferred to use a molar excess of the cyclodextrin in relation to detergent in order to substantially completely sequester the surfactant and reverse the effect of the detergent. The cyclodextrin will be added in a volume of from about 0.1 to 5, usually 0.5 to 3 times the volume of the sample and liquid single reagent. Conveniently the cyclodextrin is prepared as an aqueous solution, referred to as a "start" solution, in a concentration of from about 1.2 to 10 times the concentration desired in the assay medium, generally about 1.5 to 5.0 times the desired final concentration. The start solution can be prepared in any buffer suitable for use in an assay or suitable when mixed with the solution containing the other components of the assay medium. Generally satisfactory start solutions can be prepared as aqueous solutions containing from about 0.5% to about 5.0%, usually about 1.0 to about 2.0% (w/v) cyclodextrin.

While use of a cyclodextrin is preferred to reverse the surfactant-induced inhibition of complex formation, other surfactant-inhibition agents also find use. For example, the surfactant inhibition can be reversed by the addition of an excess of protein. Alternatively, some surfactants are known to neutralize the effects of other surfactants. See, for example, Dimitriadis, *Anal. Bioch.* (1979) 98:445-451.

The liquid single reagent composition will vary widely, depending upon the nature of the reagents and the desired ratio of the complementary specific binding pair members. Also, the amount of other materials may affect the concentration of the sbp members and vice versa. Each of the complementary members of the specific binding pair will generally be present in $5 \times 10^{-6}$ to 0.1% by weight of dry ingredients (excluding fillers and excipients). In the case of enzyme labels, if substrate is present, it will be present in an amount of about 1 to 15%. Buffer will usually comprise 5 to 30%. Finally, the surfactant will be present in an amount of from about 10 to 30%.

A preferred embodiment for determining the amount of analyte present in a sample comprises combining a liquid single reagent comprising an enzyme-analyte conjugate, an anti-analyte antibody, and a reaction-inhibiting amount of a surfactant, with the sample, enzyme substrate and a sufficient amount of a cyclodextrin to initiate complex formation. The enzyme-catalyzed reaction rate during the assay measurement differs, usually decreases, when the enzyme conjugate is bound by antibody, e.g. glucose-6-phosphate dehydrogenase (G6PDH) or $\beta$-galactosidase present as enzyme donor (ED) and enzyme acceptor (EA) fragments. The cyclodextrin is not added to the single reagent components prior to addition of the sample. The rate of enzyme-catalyzed reaction is determined as indicative of the amount of analyte present in the sample. Assays which utilize G6PD-analyte conjugates are described in U.S. Pat. No. 3,817,837. Assays which utilize $\beta$-galactosidase ED-analyte conjugates are described hereinafter and in U.S. Pat. No. 4,708,929.

The $\beta$-galactosidase complementation assay method utilizes a liquid single reagent comprising in a reaction buffer, a $\beta$-galactosidase ED-analyte conjugate, an anti-analyte antibody and a surfactant in a concentration sufficient to inhibit complex formation between analyte and anti-analyte antibody and complementation between ED and EA. The single reagent may additionally contain a $\beta$-galactosidase EA and/or enzyme substrate. Alternatively, those components which are not specific for a particular analyte can be provided as a second, common reagent. In the case of physiological fluids, other than the removal of particulates, no pretreatment of the sample will usually be performed for purposes of the instant assay method.

The method comprises combining a liquid single reagent comprising a $\beta$-galactosidase ED-analyte conjugate, an anti-analyte antibody, a reaction-inhibiting amount of a surfactant, and optimally as part of the single reagent or separately, a $\beta$-galactosidase EA and enzyme substrate with the sample and a cyclodextrin. The cyclodextrin is added to the liquid single reagent in the presence of sample, either together with or following addition of sample. The $\beta$-galactosidase-catalyzed substrate transformation to product is determined in a preselected time period as indicative of the amount of analyte present in the sample.

The enzyme donor and enzyme acceptor are partial sequences of $\beta$-galactosidase. Either partial sequence may be mutated to facilitate preparation of the sequence, attachment of an analyte or the like. The enzyme acceptor and enzyme donor analyte conjugate are characterized by forming an active enzyme complex when brought together. When the enzyme donor conjugate is bound to anti-analyte antibody the observed enzyme activity is different from that observed in the absence of anti-analyte antibody. Thus, the availability of antibody to bind with enzyme donor conjugate will vary with the amount of analyte in the medium.

$\beta$-Galactosidase enzyme donors and acceptors are described in U.S. Pat. No. 4,708,929, which disclosure is incorporated herein by reference, as are analytes and enzyme donor-analyte conjugates. Copending U.S. patent application, Serial No. 151,412 filed Feb. 2, 1988, describes reaction conditions and reagents for complementation assays. The conditions of the assay described in that application are applicable to the subject invention.

The assay conditions and the reaction buffer used provide for complementation between enzyme donor and enzyme acceptor. In general, physiological buffers such as phosphate buffered saline, tris buffer and like buffers are useful. The ionic strength is not critical. A preferred buffer comprises about 100 mM to about 300 mM $NaPO_4$, about 5 mM to about 10 mM EGTA, and about 10 mM to 20 mM $NaN_3$ having a pH of between 6 and 8. The temperature for the assay will usually be at least about 20° C., preferably elevated, but below 60° C. Enzyme assays are generally conducted at between room temperature (25° C.) to less than about 40° C., most usually about 37° C. The assays are performed at atmospheric pressure.

The concentration of enzyme donor conjugates in the assay medium will usually be in the range of about 1 nM to about 60 nM, more usually about 5 nM to about 50 nM, most usually 10 to 25 nM. The enzyme acceptor will usually be in substantial molar excess. The EA concentration will vary from about 0.5 to about 5.0 $\mu$M, usually about 1 to about 2 $\mu$M. The molar ratios of enzyme donor conjugate to enzyme acceptor will usually be 1:30 to 1:80, more usually 1:50 to 1:60. The concentration of the enzyme donor-analyte conjugate will usually exceed the highest concentration of the analyte anticipated to be encountered in the sample.

The optimal ratio of ED-analyte conjugate and anti-analyte antibody will be determined in the presence of EA so as to span the range of assay ligand and also to minimize the background activity. The response of the enzyme-catalyzed reaction rate to analyte concentration in relation to background level is optimized.

The ratio of the concentration of ED-analyte conjugate and anti-analyte antibody will be such as to substantially achieve minimum enzyme rate under assay conditions, while maintaining linearity of the rate varying with analyte concentration over the desired assay range. Usually the concentrations of antibody and conjugate will be within at least 85%, more usually within at least 95% of the concentration necessary to optimize conditions.

Varying amounts of sample can be used. When the sample is serum, usually the sample will comprise from about 1% to about 10% of the volume of the assay medium, more usually about 2% to about 5%.

An enzyme substrate is employed that when cleaved by the enzyme results in a change in the amount of light absorbance (optical density) or emission of the assay medium. That is, cleavage of the substrate results in the appearance or disappearance of a colored or fluorescent product. Preferred enzyme substrates include ortho-nitrophenyl galactoside (ONPG) and chlorophenylred-$\beta$-galactoside (CPRG). ONPG and CPRG absorbance values are measured at 420 nm and 574 nm, respectively. ONPG, CPRG and other comparable enzyme substrates are commercially available. ONPG will generally be used at a concentration of from about 0.5 to about 2.0 mg/ml, more usually about 1.0 to about 1.5 mg/ml. Using ONPG or CPRG, the assay medium will conveniently be incubated for from about 1 to 10 min., usually 1 to 4 min., most usually 1 to 3 min. following addition of the cyclodextrin to a first determination of optical density. There will usually be 1 to 10, more usually 3 to 8, most usually 3 to 6 min., between the first and second reading.

To perform the assay, a liquid single reagent is prepared. The sample may be combined with the single reagent to form an assay medium and incubated at about 37° C. for from about 10 to about 30 min. prior to addition of the cyclodextrin or the cyclodextrin may be added at the same time as the sample. Following addition of the cyclodextrin start solution and any assay components not present in the liquid single reagent, the assay medium is incubated for a predetermined period of time. The difference in the optical density of the assay medium at two preselected time points is determined as indicative of the amount of analyte in the sample. The amount of enzyme activity in the medium is determined as indicative of the amount of analyte present in the sample in accordance with standard techniques for measuring $\beta$-galactosidase activity.

A convenient way of calibrating the assay is to prepare a graph of the rate of optical density change versus concentration using control samples having known analyte concentrations. The analyte control samples are conveniently prepared solutions having 0% analyte and having an infinite concentration of analyte, i.e. an analyte concentration such that further addition of analyte does not affect the reaction rate. Desirably, one or more analyte controls of intermediate concentration, conveniently in the normal range of the sample, will also be used to prepare a standard curve.

A kit containing reagents facilitating the present invention is also contemplated. The kit comprises the complementary members of a specific binding pair and a surfactant in a first container, where usually the specific binding pair is analyte/anti-analyte antibody. A cyclodextrin is provided in a second container. For use in a complementation assay, the first container comprises ED-analyte conjugate, anti-analyte antibody, and a surfactant. The first container may additionally contain other reagents present in the assay mixture such as enzyme substrate and EA. Conveniently however, the common reagents useful for a plurality of analytes are present in a third container or with the cyclodextrin. The kit may additionally comprise one or more analyte controls at varying concentrations in the anticipated sample concentration range.

The reagents can be formulated in liquid form or in dry form as a powder or a unit dosage tablet containing a quantity of reagents suitable for assay of one sample. The dry reagent(s) may contain buffer salts or buffer can be provided for reconstituting the dry reagent. The dry reagent may be formulated with conventional additives such as stabilizers, drying agents, excipients and the like.

The following examples are offered by way of illustration and not by way of limitation.

EXPERIMENTAL
Example 1 - T4 Assay

Reagents

T4 Reconstitution Buffers

-continued
EXPERIMENTAL
Example 1 - T4 Assay

| ED Buffer | |
|---|---|
| 60 mM $PO_4^{3-}$ | Buffer |
| 19.4 mM | $NaN_3$ |
| 10 mM | EGTA |
| 0.416 mM | ANS |
| | pH = 7.0 |
| EA Buffer | |
| 90 mM $PO_4^{3-}$ | Buffer |
| 19.4 mM | $NaN_3$ |
| 4.8 mM | $Mg(OAc)_2.4H_2O$ |
| 10 mM | EGTA |
| | pH = 7.6 |
| Triton X-301 | As detergent |
| ONPG | As enzyme substrate |
| EA22 | Described in U.S. Pat. No. 4,708,929 |
| $ED_4$-T4 | Prepared from Thyroxine derivative and $ED_4$, as described in U.S. Pat. No. 4,708,929 |
| Monoclonal anti-T4 antibodies | |
| $\beta$-Cyclodextrin | Available commercially from Sigma Chemical Company |
| EGTA | Ethylene-bis-oxy-ethylenenitrilo tetraacetic acid |

Assay Procedure

A 5 ml reagent solution was prepared by mixing the following components.
3323 $\mu$l of ED buffer
312.5 $\mu$l of a 4% Triton X-301 solution
(dilution of 20% reagent stock with ED buffer to obtain 4% solution)
750 $\mu$l of 10 mg/ml stock solution of ONPG in ED buffer
102.4 $\mu$l of 6 × $10^{-5}$ M EA22
200 $\mu$l of a 1:300 dilution of 1.35 × $10^{-4}$ M $ED_4$-T4 in ED buffer
312.5 $\mu$l of a 1:100 dilution of anti-T4 Antibody in ED buffer A 1% $\beta$-cyclodextrin "start" solution was made using 0.50 g in 50 ml of EA buffer. 10 $\mu$l of a serum calibrator ranging in concentration from 0, 2.5, 5, 10, 20 24, 200 $\mu$g/dl was added to 100 $\mu$l of the reagent solution and incubated 15 min. at 37° C. (oven incubator). The reaction was initiated in a Baker Encore Chemistry Analyzer by addition of 200 $\mu$l of $\beta$-cyclodextrin start solution. Absorbance was read at 420 nm at 360 and 540 sec. following addition of cyclodextrin.

Results

The results are illustrated in Table 1. As used in the table, the percentage of modulation is the difference between any two calibrators; i.e., the net difference divided by the rate of the higher calibrator.

TABLE 1

| T4 ($\mu$g/dl) | $\Delta$540-360 sec (mA) | % Modulation |
|---|---|---|
| 0 | 64 | 0 |
| 2.5 | 72 | 11.11 |
| 5 | 80 | 20.00 |
| 10 | 96 | 33.33 |
| 20 | 118 | 45.76 |
| 24 | 119 | 46.22 |
| 200 | 178 | 64.04 |
| $\infty$ | 211 | 69.76 |

As shown in Table 1, the assay is useful between concentrations of 0 and 20 $\mu$g/dl of T4 in the patient sample.

Example 2 - B12 Assay

Reagents

B12 Assay Liquid Single Reagent Solution $ED_4$-$B_{12}$ Conjugate - 3 nM
Intrinsic Factor - 1:6000 dilution
Substrate (CPRG) - 1.3 mg/ml
Triton - 0.2%, 0.4% or 0.8% in ED buffer as described in Example 1

Common Reagent Solution $EA_{22}$ - $1.0 \times 10^{-6}$ M
β-cyclodextrin - 1.0% in EA buffer as described in Example 1

Assay Procedure

10 μl sample (0 or 1 μg/ml analyte control sample) was mixed with 100 μl of single reagent solution and 150 μl of common reagent solution. The absorbance change was read at 60 and 180 seconds following addition of cyclodextrin.

Results

The results are shown in Table 2. As used in the table, the net rate is defined as the difference in zero and high calibrator rate, and percentage inhibition is defined as the ratio of net rate to the high calibrator rate.

TABLE 2

| Triton Conc. | Zero Calib. | High Calib. | Net. Rate | % Inhibition |
|---|---|---|---|---|
| In the Absence of Cyclodextrin ||||| 
| 0% | 42 | 161 | 119 | 73.9% |
| 0.2% | −25 | −21 | N/A | N/A |
| 0.4% | −55 | −54 | N/A | N/A |
| In the Presence of Cyclodextrin |||||
| 0% | 11 | 79 | 68 | 86.1% |
| 0.2% | 35 | 137 | 102 | 74.5% |
| 0.4% | 28 | 112 | 84 | 75.0% |

The results indicate that Triton X-301 concentrations greater than about 0.2% effectively inhibited complementation.

Example 3 - Theophylline Assay

Reagents

Theophylline Liquid Single Reagent Solution

Prepared in 0%, 0.2%, or 0.3% Triton X-301: [$ED_4$-theophylline conjugate]=46 nm [Anti-theophylline antibody]=1:900 dilution
Substrate CPRG (chlorophenol red galactoside)=0.5 mg/ml

Common Reagent Solution ($EA_{22}$)=1.2 μM containing 0, 0.5, 1 or 2% β-cyclodextrin (β-cd)

Sample zero or 200 μg/ml of analyte control

Assay Procedure

10 μl sample was mixed with 200 μl theophylline single reagent solution along with 150 μl of common reagent. The change in absorbance was read at 4 and 8 minutes.

Results

The results are shown in Table 3 which illustrate the values for 0 and 200 μg/ml (infinite dose) calibrators with 0, 0.2 and 0.3% Triton surfactant. The percentage of inhibition of the reaction rate was calculated as follows. The change in optical density of a 0% analyte control sample was subtracted from the change in optical density of a 100% analyte control sample. That number was divided by the change in optical density for a 100% analyte control to determine the percentage of inhibition. Each Triton concentration has two charts. One chart is for rates at 0 dose in the presence of varying cyclodextrin concentrations [CD]; the other is for an infinite dose.

TABLE 3

| [β-cd] | 240 sec | 480 sec | Δ480-240 | % Inhibition |
|---|---|---|---|---|
| 0% Triton X-301 zero dose |||||
| 0% | 267 | 975 | 708 | 0.47 |
| 0.50% | 205 | 754 | 549 | 0.51 |
| 1% | 158 | 566 | 408 | 0.52 |
| 2% | 98 | 303 | 205 | 0.59 |
| 0% Triton X-301 200 dose |||||
| 0% | 264 | 1799 | 1335 | |
| 0.50% | 388 | 1507 | 1119 | |
| 1% | 299 | 1149 | 850 | |
| 2% | 193 | 695 | 502 | |
| 0.2% Triton X 301 zero dose |||||
| 0% | 68 | 93 | 25 | 0.34 |
| 0.50% | 216 | 682 | 466 | 0.52 |
| 1% | 196 | 677 | 481 | 0.53 |
| 2% | 156 | 474 | 318 | 0.55 |
| 0.2% Triton X-301 200 dose |||||
| 0% | 102 | 140 | 38 | |
| 0.50% | 421 | 1385 | 964 | |
| 1% | 384 | 1416 | 1032 | |
| 2% | 290 | 991 | 701 | |
| 0.3% Triton X-301 zero dose |||||
| 0% | 72 | 79 | 7 | 0.56 |
| 0.50% | 169 | 332 | 163 | 0.55 |
| 1% | 222 | 734 | 512 | 0.55 |
| 2% | 181 | 540 | 359 | 0.56 |
| 0.3% Triton X-301 200 dose |||||
| 0% | 99 | 115 | 16 | |
| 0.50% | 333 | 697 | 364 | |
| 1% | 443 | 1569 | 1126 | |
| 2% | 327 | 1137 | 810 | |

As shown in the table, 0.2% to 0.3% Triton X-301 was effectively neutralized by 1% to 2% β-cyclodextrin.

As shown by the foregoing examples, the present assay method is fast and accurate, and requires minimal manipulations and a shortened incubation period. The formulation of the reagent solution is particularly convenient, as the user need only mix a few reagents with the sample to initiate the assay. The liquid single reagent mixture is also suitable for use in autoanalyzers.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for using a preformed liquid single reagent in an assay of an analyte, wherein said analyte is a member of a specific binding pair comprising said analyte and a binding protein, wherein said liquid single reagent comprises (1) a β-galactosidase enzyme donor-analyte conjugate, referred to herein as ED-analyte conjugate, wherein said ED-analyte conjugate is capable of forming an active enzyme having β-galactosidase activity when combined with a β-galactosidase enzyme acceptor, referred to herein as EA, (2) said binding protein, and (3) an amount of a surfactant sufficient to inhibit binding between said analyte and said binding protein, said method comprising:

combining said liquid single reagent with an amount of a cyclodextrin sufficient to overcome inhibition of binding of said binding protein to said analyte, thereby allowing formation of said complex.

2. The method of claim 1 wherein said liquid single reagent additionally comprises a β-galactosidase enzyme acceptor (EA).

3. A method for determining the amount of analyte present in a sample, wherein said analyte is a member of a specific binding pair comprising said analyte and a binding protein, said method comprising:

(a) combining to form an assay medium (1) a β-galactosidase enzyme donor/analyte conjugate, referred to herein as ED-analyte conjugate, wherein said ED-analyte conjugate is capable of forming an active enzyme having β-galactosidase activity when combined with a β-galactosidase enzyme acceptor, referred to herein as EDA, (2) said binding protein, (3) said β-galactosidase enzyme acceptor, (4) enzyme substrate reactive with β-galactosidase, (5) an amount of surfactant sufficient to inhibit formation of a complex between said analyte and said binding protein, (6) said sample, and (7) a cyclodextrin which is added in an amount sufficient to reverse inhibition of binding between said analyte and said binding protein, with the provisos that (1) EA and Ed-analyte conjugate are combined in said assay medium in the presence of said surfactant and (2) cyclodextrin is not added to said assay medium prior to addition of said sample to said assay medium; and (b) determining rate of β-galactosidase activity on said substrate as indicative of the amount of analyte present in said sample.

4. The method of claim 3 wherein said specific binding pair is antigen/antibody.

5. The method of claim 4 wherein said antigen is said analyte.

6. The method of claim 3 wherein said sample is serum, whole blood, plasma, or urine.

7. The method of claim 3 wherein said sample is serum which comprises about 1% to about 10% of the volume of said assay medium.

8. The method of claim 3 wherein said surfactant is a nonionic detergent.

9. The method of claim 8 wherein said nonionic detergent comprises a polyoxyethylene p-t-octyl phenol.

10. The method of claim 3 wherein said cyclodextrin is β-cyclodextrin.

11. A method for determining the amount of analyte present in a serum sample, comprising:

(a) combining the following reagents in the order given:

(i) a liquid single reagent comprising a β-galactosidase enzyme donor/analyte conjugate, referred to herein as ED-analyte conjugate, wherein said ED-analyte conjugate is capable of forming an active enzyme having β-galactosidase activity when combined with a β-galactosidase enzyme acceptor, referred to herein as EA; an analyte receptor; and a surfactant in an amount sufficient o inhibit binding between said analyte and said analyte receptor;

(ii) said β-galactosidase enzyme acceptor;

(iii) a β-galactosidase enzyme substrate;

(iv) said sample; and (v) a sufficient amount of a cyclodextrin to reverse inhibition of binding between said analyte receptor and said analyte; and (b) determining a change in light absorption or emission by a product of β-galactosidase-catalyzed reaction of said substrate as indicative of the amount of analyte present in said sample.

12. The method of claim 11 wherein said analyte is thyroxine.

13. The method of claim 11 wherein said enzyme substrate comprises ortho-nitrophenyl-β-galactoside (ONPG).

14. A method for determining the amount of analyte present in a serum sample, comprising:

(a) combining the following substances in the order given:

(i) a liquid single reagent comprising a β-galactosidase enzyme donor/analyte conjugate, referred herein as ED-analyte conjugate, wherein said ED-analyte conjugate is capable of forming an active enzyme having β-galactosidase activity when combined with a β-galactosidase enzyme acceptor, referred to herein as EA; an analyte receptor; said β-galactosidase enzyme acceptor; a β-galactosidase enzyme substrate; and a surfactant in an amount sufficient to inhibit binding between said analyte and said analyte receptor;

(ii) said sample; and (iii) a sufficient amount of a cyclodextrin to reverse inhibition of binding between said analyte receptor and said analyte; and (b) determining change in light absorption or emission by a product of a β-galactosidase-catalyzed reaction of said substrate as indicative of the amount of analyte present in said sample.

15. The method of claim 14 wherein said analyte is vitamin B12 or theophylline.

16. The method of claim 14 wherein said enzyme substrate comprises chlorophenolred-β-galactoside (CPRG).

17. A method for determining the amount of thyroxine, referred to herein as T4, present in a serum sample comprising in the following order:

(a) incubating a solution comprising from about 10 mM to about 25 mM of a β-galactosidase enzyme donor-T4 conjugate, referred to herein as ED-T4 conjugate, wherein said ED-T4 conjugate is capable of forming an active enzyme having β-galactosidase activity when combined with a β-galactosidase enzyme acceptor, referred to herein as EA, from about 1.0 μM to 2.0 μM EA, from about 0.2% to bout 0.5% (w/w) of a polyoxylene p-t-octyl phenol, anti-T4 antibody, and from about 1 mg/ml to about 2 mg/ml O-nitrophenyl-β-galactoside with said sample for about 10 to 30 min. at 37° C. to form an assay medium;
(b) adding a cyclodextrin solution with said assay medium to a final concentration of from about 0.5% to 1.2% (w/w);
(c) incubating said assay medium for about 1 min. to about 3 min. at about 37° C.;
(d) determining the optical density of said assay medium;
(e) incubating said assay medium for about 3 min. to about 6 min., at about 37° C.;
(f) determining the optical density of said assay medium;
(g) comparing the difference in the optical density of steps (d) and (f) to the difference in optical density of a sample having a known concentration of T4.

18. A method for determining the amount of an analyte present in a serum sample comprising in the following order:
(a) incubating a solution comprising from about 5 nM to about 50 nM of a β-galactosidase enzyme donor-analyte conjugate, referred to herein as ED-analyte conjugate, wherein said ED-analyte conjugate is capable of forming an active enzyme having β-galactosidase activity when combined with a β-galactosidase enzyme acceptor, referred to herein as EA, from about 1 μM to about 2 μM EA, from about 0.2% to bout 1.0% (w/w) of a polyoxylene-p-t-octyl phenol, analyte receptor and from about 0.5 mg/ml to about 1.5 mg/ml O-nitrophenyl-β-galactoside with said sample and a cyclodextrin in a concentration of from about 0.5% to about 2% (w/w) to form an assay medium;
(b) incubating said assay medium for about 1 min. to about 4 min. at about 37° C;
(c) determining the optical density of said assay medium;
(d) incubating said assay medium for about 3 min. to about 8 min. at about 37° C.;
(e) determining the optical density of said assay medium;
(f) comparing the difference in the optical density of steps (c) and (e) to the difference in optical density of a sample having a known concentration of analyte.

19. The method of claim 18 wherein said analyte is vitamin $B_{12}$ and said analyte receptor is intrinsic factor.

20. The method of claim 18 wherein said analyte is theophylline and said analyte receptor is anti-theophylline antibody.

21. A liquid single reagent for assaying an analyte, wherein said analyte is a member of a specific binding pair comprising said analyte and a binding protein, said reagent comprising an amount of surfactant sufficient to inhibit binding between said analyte and said binding protein; a β-galactosidase enzyme donor/analyte conjugate referred to herein as ED-analyte conjugate, wherein ED-analyte conjugate is capable of forming an active enzyme having β-galactosidase activity when combined with a β-galactosidase enzyme acceptor, referred to herein as EA; and said binding protein.

22. The liquid single reagent of claim 21 wherein said specific binding pair is antigen/antibody.

23. The liquid single reagent of claim 22 wherein said analyte is an antigen and said complementary member of said specific binding pair is an antibody.

24. The liquid single reagent of claim 21 wherein said surfactant is present at from about 0.1 to about 1% (w/w).

25. The liquid single reagent of claim 21 wherein said surfactant is a nonionic detergent.

26. The liquid single reagent of claim 21 wherein said reagent additionally comprises EA or enzyme substrate.

27. A kit, comprising:
(1) a first container comprising a liquid single reagent of claim 21; and
(2) a second container containing a cyclodextrin.

28. The kit of claim 27 wherein said specific binding pair comprises ED-analyte conjugate and anti-analyte antibody.

29. The kit of claim 27 wherein said first container additionally comprises EA and enzyme substrate.

30. The kit of claim 27 wherein said kit additionally comprises a third container comprising EA and enzyme substrate.

31. The kit of claim 27 wherein said kit additionally comprises at least one analyte control.

32. The kit of claim 27 wherein said liquid single reagent is present in said kit in dry form.

33. The kit of claim 32 wherein said liquid single reagent comprises a quantity of reagents 34. The kit of claim 33 wherein said kit additionally comprises in a separate container a buffer solution.

* * * * *

UNITED STATES PATENT AND TRADEMARK OFFICE
CERTIFICATE OF CORRECTION

PATENT NO. : 5,032,503

DATED : July 16, 1991

INVENTOR(S) : P.L. Khanna et al.

It is certified that error appears in the above-identified patent and that said Letters Patent is hereby corrected as shown below:

Title page item [54], replace "AIR" with --AN-- in the title.

Title page item [75], replace "Davis" with --Concord--.

In column 1, replace "AIR" with --AN-- in the title.
Column 11:
In Claim 3, line 33, replace "EDA" with --EA--.

In Claim 3, line 42, replace "Ed" with --ED--.
Column 12:
In Claim 11, line 9, replace "o" with --to--.
Column 12:
In Claim 17, line 66, replace "bout" with --about--.

Signed and Sealed this

Fourth Day of May, 1993

Attest:

MICHAEL K. KIRK

*Attesting Officer*     *Acting Commissioner of Patents and Trademarks*